(12) United States Patent
Gosine et al.

(10) Patent No.: US 10,512,847 B2
(45) Date of Patent: Dec. 24, 2019

(54) MOTION DETECTING BALANCE, COORDINATION, MOBILITY AND FITNESS REHABILITATION AND WELLNESS THERAPEUTIC VIRTUAL ENVIRONMENT

(71) Applicant: Rutgers, The State University of New Jersey, New Brunswick, NJ (US)

(72) Inventors: Robb Gosine, Bellerose Manor, NY (US); Judith Deutsch, Millburn, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 97 days.

(21) Appl. No.: 15/757,077

(22) PCT Filed: Aug. 31, 2016

(86) PCT No.: PCT/US2016/049695
§ 371 (c)(1),
(2) Date: Mar. 2, 2018

(87) PCT Pub. No.: WO2017/040658
PCT Pub. Date: Mar. 9, 2017

(65) Prior Publication Data
US 2019/0176043 A1  Jun. 13, 2019

Related U.S. Application Data

(60) Provisional application No. 62/213,263, filed on Sep. 2, 2015.

(51) Int. Cl.
*G09B 19/00* (2006.01)
*A63F 13/67* (2014.01)
(Continued)

(52) U.S. Cl.
CPC ............. *A63F 13/67* (2014.09); *A61B 5/11* (2013.01); *A61B 5/1114* (2013.01);
(Continued)

(58) Field of Classification Search
CPC ............. G09F 19/00; A63F 2300/8082; A63F 2024/0096; A63F 24/00; A63B 71/00
See application file for complete search history.

(56) References Cited

U.S. PATENT DOCUMENTS

2010/0034404 A1   2/2010   Dent
2013/0171596 A1   7/2013   French
(Continued)

FOREIGN PATENT DOCUMENTS

WO   2006014810 A2   2/2006
WO   2014124002 A1   8/2014

*Primary Examiner* — Omkar A Deodhar
(74) *Attorney, Agent, or Firm* — Fox Rothschild LLP

(57) ABSTRACT

Systems and methods for providing a Digital Health Platform ("DHP") game for execution on a computing device. The methods comprise: running code on the computing device to facilitate lower extremity tracking in a low light condition and the provision of the DHP game having a virtual environment in which a person is to interact with at least one virtual object; using the code to obtain tracked data defining tracked movements of at least the person's lower extremities as the person plays the DHP game in the low light condition; increasing an accuracy of at least position data contained in the tracked data by performing coarse filtering operations and fine filtering operations using the position data; and recreating the person's lower extremity movement in the virtual environment using the position data which has been coarse and fine filtered.

23 Claims, 13 Drawing Sheets

(51) Int. Cl.
*A61B 5/11* (2006.01)
*G06K 9/00* (2006.01)
*A63F 13/213* (2014.01)
*A63F 13/212* (2014.01)
*G16H 20/30* (2018.01)
*G16H 50/30* (2018.01)
*A63B 24/00* (2006.01)
*G16H 40/63* (2018.01)
*G16H 40/67* (2018.01)
*G16H 40/40* (2018.01)

(52) U.S. Cl.
CPC ........ *A63B 24/0075* (2013.01); *A63F 13/212* (2014.09); *A63F 13/213* (2014.09); *G06K 9/00342* (2013.01); *G16H 20/30* (2018.01); *G16H 50/30* (2018.01); *A63B 2024/0065* (2013.01); *A63F 2300/1012* (2013.01); *A63F 2300/1087* (2013.01); *A63F 2300/6027* (2013.01); *A63F 2300/8005* (2013.01); *A63F 2300/8082* (2013.01); *G16H 40/40* (2018.01); *G16H 40/63* (2018.01); *G16H 40/67* (2018.01)

(56) References Cited

U.S. PATENT DOCUMENTS

2013/0303286 A1 11/2013 Ferguson et al.
2013/0342691 A1 12/2013 Lewis et al.
2015/0120023 A1 4/2015 Terrell, II

MOTION DETECTING BALANCE, COORDINATION, MOBILITY AND FITNESS REHABILITATION AND WELLNESS THERAPEUTIC VIRTUAL ENVIRONMENT

CROSS-REFERENCE TO RELATED APPLICATIONS

The present application claims the benefit of U.S. Provisional Patent Application 62/213,263 filed Sep. 2, 2015 and International Patent Application No. PCT/US2016/049695 filed on Aug. 31, 2016. The contents of these Patent Applications are incorporated herein by reference.

FIELD OF THE INVENTION

This document relates generally to systems and methods for providing a motion detection balance, mobility and fitness game in which a person's movements are examined, tracked and reported.

BACKGROUND OF THE INVENTION

Clinical adoption of Virtual Reality ("VR") rehabilitation faces several hurdles. Two of these are equipment costs and the VR interface.

SUMMARY

The present disclosure concerns systems and methods for providing a Digital Health Platform ("DHP") game for execution on a computing device. The DHP game can include, but is not limited to, a Motion Detection Balance, Mobility and Fitness ("MDBMF") game. The methods comprise: running code on the computing device to facilitate lower extremity tracking in a various light conditions (especially in low light conditions) and the provision of the DHP game having a virtual environment in which a person is to interact with at least one virtual object; using the code to obtain tracked data defining tracked movements of at least the person's lower extremities as the person plays the DHP game in multiple light conditions (particularly in the low light conditions); increasing the accuracy of at least position data contained in the tracked data by performing combinations of sequential coarse filtering operations and fine filtering operations using the position data; and recreating the person's lower extremity movement in the virtual environment using the position data which has been coarse and fine filtered.

In some scenarios, an open source code development kit is used to implement the code. The tracked data comprises video data, heart rata data, eye movement data and/or brain electrical activity data in addition to the position data. The heart rate data may be obtained using infrared technology of a depth camera, which acquires infrared data for at least one of a person's forehead, a person's checks, and a person's jaw line. The coarse and fine filtering operations for the motion or position data comprise smoothing, correction, prediction, maximum deviation and jitter radius operations, where the jitter radius is a radius of measure taken from the assumed true point and extends to a calculated radius that includes permissible deviations from the true point and will encompass the predicted points and trajectories in still and in motion.

In those or other scenarios, the coarse and fine filtering operations comprise: obtaining a positional xyz data point of where the person's body part is expected to be located in a multi-dimensional space; obtaining a trajectory prediction for the person's body part; determining if a detected movement match a predicted movement; mapping the detected movement as a true and accurate trajectory of the person's body part if the detected movement matches a predicted movement; and disregarding any tracked data that indicates a deviation of a certain degree from the true and accurate trajectory.

In those or yet other scenarios, the methods further comprise: determining a difference between a first infrared pattern defined by the tracked data and a second infrared pattern defined by the tracked data; and determining the person's current body temperature using the determined difference between the first and second infrared patterns. Additionally or alternatively, the methods further comprise: calculating a first variation in density between adjacent pixels of first infrared data associated with a first data frame and a second variation in density between adjacent pixels of a second infrared data associated with a second data frame; determining a difference between the first and second variations; and determining the person's current body temperature using the determined difference between the first and second variations.

DESCRIPTION OF THE DRAWINGS

The present solution will be described with reference to the following drawing figures, in which like numerals represent like items throughout the figures.

DETAILED DESCRIPTION

Figure 1:
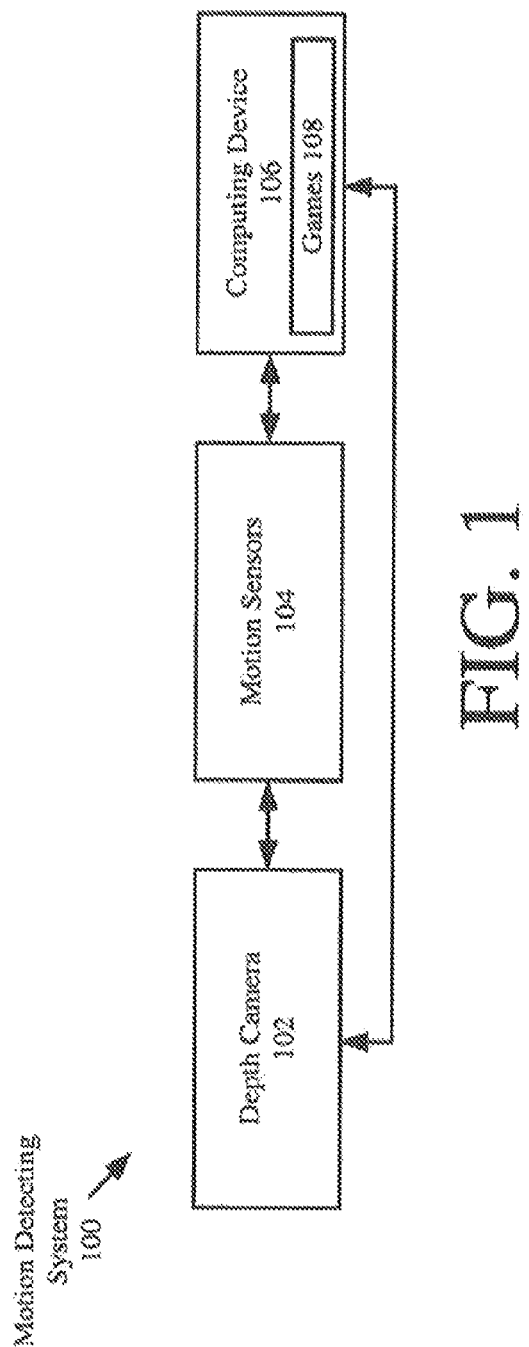
FIG. 1 is a perspective view of an exemplary system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes, which come within the meaning and range of equivalency of the claims, are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

INTRODUCTION

VR and serious games are used herein to (a) deliver therapeutic interventions in a clinical setting and remotely in a user's home, (b) examine the patient's performance, and/or (c) track the patient's progress over time. The VR rehabilitation presents a Virtual Environment ("VE") wherein the user performs a task that is repeated and progressed over time. The VE may also incorporate a game designed to address a particular area for improvement, such as stepping, walking, dancing, doing sports drills, reaching and/or grasping. Depending on the game design, the progress is tracked manually or recorded in the gameplay.

It has been found that VR Games ("VRGs") can provide a satisfactory complement to traditional physical therapy. VRGs have been developed to provide physical rehabilitation by challenging balance and coordination as well as promoting activity. VRG implementation ranges from off-the-shelf game systems with minimal or no adaptation to adapted commercial products using customized or proprietary hardware and/or software. A problem that typically arises is the cost of acquiring and developing the VR, the associated equipment, and an acceptable VR environment that engages the user. Further, with off-the-shelf games, there are issues with customization to the user's abilities.

In some scenarios, Microsoft® Windows (e.g., Windows 7 (or "Win7") or Windows 10 (or "Win10")) is used as the core Operating System ("OS"). In this case, stepping games were created that are deployable on over 70% of the desktop and laptop market, which reduces the initial capital investment by the clinician. By utilizing C# which is freely available in MS Visual Studio Express and the Microsoft Kinect® Software Development Kit ("SDK"), the clinician is presented with a package that is low in cost and easily adaptable to their needs. Microsoft Kinect® SDK is an open source software program. The term "open source", as used herein, refers to any software program or application whose source code is made available for use or modification as users or other developers see fit. The term "source code", as used herein, refers to a part of software that can be manipulated to change how a software program or application works. The present invention is not limited to open source applications. Open source software is simply used in some scenarios, and is not a requirement for the implementation of the present systems and methods. The C# code is written to encourage a beginner programmer to jump right in and get started. By using the MS Windows Presentation Foundation ("WPF") interface (packaged with Visual Studio), the beginner programmer/clinician has ready access to a Graphical User Interface ("GUI") that enables him(her) to see the layout of his(her) project.

Deploying the games as a managed-open-source project, allows the provision of the source code to the wider community of Kinect® enthusiasts to further develop code, while the code is still actively managed by a core group to maintain quality standards and usability. Open-source encourages the organic evolution of the code and development of solutions for a wide range of problems, as well as creates a community that can support and guide each other in a holistic manner. This can result in reduced code bugs, create a wide support network for niche projects, and engender growth not only in the Kinect® world but the VR rehabilitation world as well.

In the present document, there is described the development of sub-routines that enhance the lower extremity tracking capability of the Kinect® so that feet movement can be tracked. A solution is also described for Kinect (e.g., Kinect V1's®)) system problems with low light tracking. The sub-routines were designed to be easily implemented without taxing the OS resulting in high fidelity responsiveness. In addition, several clinician tools are included to measure displacements and velocities that can allow the clinician to track user actions and changes in performance over time. The code writes data to an appropriate storage device in an MS Excel readable format allowing the clinician to create a database of users, analyze charts of performance, perform various analytical calculations native to Excel, and publish a variety of reports. The storage device may take the form, but not limited to, a Universal Serial Bus ("USB"), hard-disk, removable media, cloud storage, network-drives, magnetic storage device, and/or an optical storage device.

Exemplary Systems

Referring now to FIG. 1, there is provided an illustration of an exemplary motion detecting system 100 (e.g., a Kinect system) designed to improve a person's balance, coordination, mobility and fitness. The motion detecting system 100 consists of a depth camera 102, a plurality of motion sensors 104 (or motion capture device or combinations thereof) and a computing device 106 (e.g., a gaming console or personal computer). The motion sensors 104 are referred to herein as a "Camera". Depth cameras and motion sensors are well known in the art. Any known or to be known depth camera and/or motion sensor can be used herein without limitation. An exemplary architecture of the computing device 106 is discussed below in relation to FIG. 2.

A plurality of games 108 is installed on the computing device 106. The games 108 are designed to facilitate rehabilitation of balance, coordination, mobility and fitness. The games 108 can be applied to a range of populations across the lifespan and with different conditions. As a person plays a game, his(her) movements are tracked by the Camera 104 of the motion detecting system 100. Information is displayed on the computing device 106 or a display coupled to the computing device (e.g., a television) that indicates the tracked motion of the person. In a health care context, a clinician can both test/examine and train the patient by selecting games as well as the games' lengths, intensities and durations (thereby making the games suitable for all skill levels and customizable for each person).

The motion detecting system 100 with integrated heart rate monitoring provides a mobile, low cost evidence based technology that motivates and tracks users' rehabilitation programs. In some scenarios, the motion detecting system 100 is configured to track a person's lower extremities (e.g., in particular a person's feet) using the depth camera 102 (e.g., the Kinect system depth camera) and Camera 104.

Figure 2:
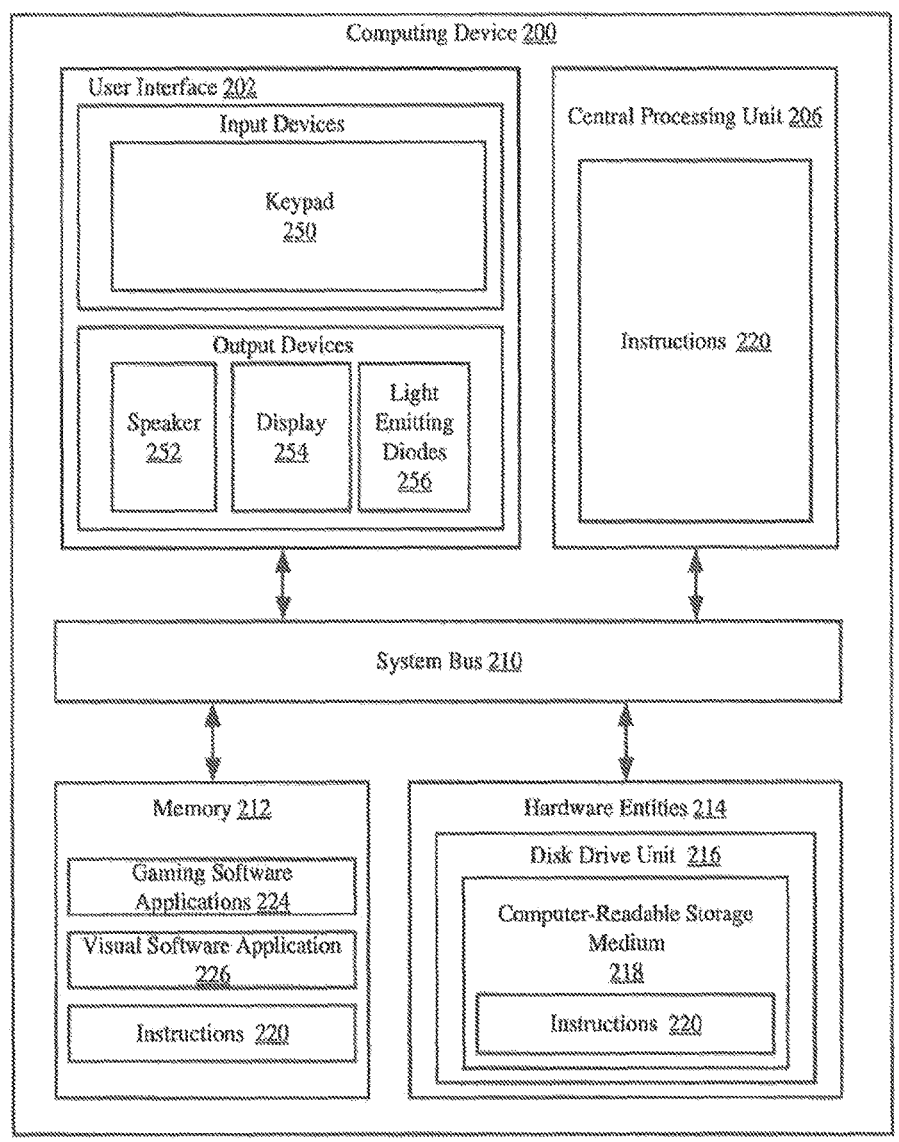
FIG. 2 is an illustration of an exemplary architecture for a computing device.

Referring now to FIG. 2, there is provided a detailed block diagram of an exemplary architecture of a computing device 200. Computing device 106 of FIG. 1 is the same as or similar to computing device 200. As such, the following discussion of computing device 200 is sufficient for understanding computing device 106.

Notably, the computing device 200 may include more or less components than those shown in FIG. 2. However, the components shown are sufficient to disclose an illustrative embodiment implementing the present invention. The hardware architecture of FIG. 2 represents one embodiment of a representative computing device configured to facilitate the provision of a gaming system in which a VE is created that graphically shows a person's tracked movements. As such, the computing device 200 of FIG. 2 implements at least a portion of a method for providing such a gaming station in accordance with embodiments of the present invention.

Some or all the components of the computing device 200 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 2, the computing device 200 comprises a user interface 202, a Central Processing Unit ("CPU") 206, a system bus 210, a memory 212 connected to and accessible by other portions of computing device 200 through system bus 210, and hardware entities 214 connected to system bus 210. The user interface can include input devices (e.g., a keypad 250, heart rate monitor 258, eye tracker 260 and brain/computer interface 262) and output devices (e.g., speaker 252, a display 254, and/or light emitting diodes 256), which facilitate user-software interactions for controlling operations of the computing device 200.

At least some of the hardware entities 214 perform actions involving access to and use of memory 212, which can be a Random Access Memory ("RAM"), a disk drive and/or a Compact Disc Read Only Memory ("CD-ROM"). Hardware entities 214 can include a disk drive unit 216 comprising a computer-readable storage medium 218 on which is stored one or more sets of instructions 220 (e.g., software code) configured to implement one or more of the methodologies, procedures, or functions described herein. The instructions 220 can also reside, completely or at least partially, within the memory 212 and/or within the CPU 206 during execution thereof by the computing device 200. The memory 212 and the CPU 206 also can constitute machine-readable media. The term "machine-readable media", as used here, refers to a single medium or multiple media (e.g., a centralized or distributed database, and/or associated caches and computer devices) that store the one or more sets of instructions 220. The term "machine-readable media", as used here, also refers to any medium that is capable of storing, encoding or carrying a set of instructions 220 for execution by the computing device 200 and that cause the computing device 200 to perform any one or more of the methodologies of the present disclosure.

In some scenarios, the hardware entities 214 include an electronic circuit (e.g., a processor and/or a graphics card) programmed for facilitating the provision of games and a VE showing tracked movements of a person (e.g., a person lower extremities) or other physiological signals (e.g., heart rate, eye movement or electrical activity of the brain). In this regard, it should be understood that the electronic circuit can access and run DHP application (e.g., gaming software applications) 224 and a visual software application 226 (e.g., MS Visual Studio Express 2012 or Unit 3D) installed on the computing device 200. The software applications 224-226 are generally operative to facilitate: the provision of examination and rehabilitation, wellness and fitness games; the tracking of a person's movements as the person plays the games; the generation of a VE in which the person's tracked movements and other physiological signals are shown with a relatively high degree of accuracy; the processing of movement data to generate analytic results; the generation of reports relating to the person's tracked movements; and/or the generation of suggested medical and/or rehabilitation plans based on the person's tracked movement and physiological signals over a given period of time. Other functions of the software applications 224-226 will become apparent as the discussion progresses.

In some scenarios, the rehabilitation, wellness and fitness gaming software applications 224 are implemented via a Kinect® based system. During testing and game play, it was found that Kinect® typically tracks motion at 30 fps (60 Hz). However, frame rate variations did occur in some instances where the frame rate dropped to 25 fps (50 Hz). This frame rate occurred in very few cases and typically at the start of data capture. Analysis of captured data showed that less than 5% of the data was captured at 25 fps. The average frame rate captured was approximately 29.75 fps. Since the games needed only to process a frame every 34 milliseconds to render the Avatar smoothly on the screen, a laptop and Kinect® SDK (e.g., Kinect® SDK 1.8 or 2.0) provided enough buffer data and capacity to render any image lag imperceptible. The term "avatar", as used herein, refers to a displayed figure representing a particular person in a computer game.

This is important when considering that any deviation of the ankle or knee joint off the lower tracking path can result in lost data forcing the Kinect® SDK to "predict" the path that the joint takes using the "captured" positions. This requires more computation and slows down the system, which in turn affects the gameplay and future motion capture perpetuating lag. By optimizing tracking for the feet, image/position capture error is reduced. The game utilizes less mathematical adjustments to achieve an acceptable level of fidelity between the actual movement of the foot and what is represented on the screen, thereby reducing the code and computational power required for an executable program.

The game development requires a three-dimensional Game Play Volume ("GPV") to provide a useable space for the user to comfortably step through the game sequences without stepping out of the Kinect's® field of vision. This volume is based on the Kinect's® horizontal and vertical viewing angles as well as the position of the camera relative to the ground. The nearest horizontal distance a user can be is 0.8 m. The farthest horizontal distance is 4.0 m. The camera has a horizontal angular field of view of 57° and a vertical angular field of view of 43° with a vertical tilt of +/−27°.

Figure 3:
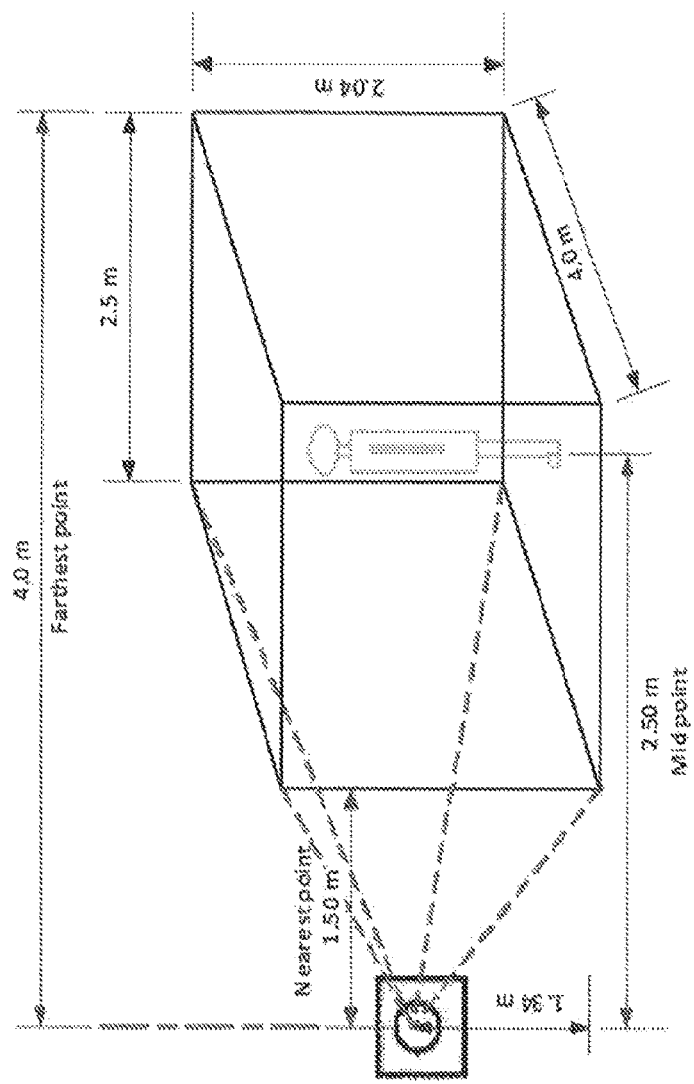
FIG. 3 is an illustration showing dimensions of a game play volume.

The GPV was designed to fit within the above parameters for a maximum user height of 2.0 m and was calibrated against real world measurement wherein fixed distances were measured in the real world and the appropriate scaling factors and mathematical conversions were used to convert the Kinect® intrinsic measure to SI units. Following this, the GPV defines the acquisition volume as 20 m$^3$ at a distance of 1.5 m from the Center of the Camera ("CoC"). Placing the user at a minimum of 1.50 m from the CoC enables the capture of a forward swing step of 45° and a vertical lift of the foot to 0.5 m measured from the floor to the top of the toes. The farthest back the user can stand from the CoC is 3.0 m, which enables the capture of a 1.0 m step back. The user can move 0.7 m to either side of the center-line of the camera at the closest or 4.0 mat the farthest with 10.0 m$^2$ of useable floor space as shown in FIG. 3.

A Volume Center ("VC") was defined as a starting point situated 2.0 m from the front of the Kinect® which allows the user to step 1 m forward/backward and 1 m left/right. Nevertheless, the code, which creates the game environment, sets the vertical distance of the camera relative to the ground. The horizontal distance relative to the VC can be manipulated to achieve an optimal GPV as may be required. Additionally, the traditional heel to heel measurement for step length was not used since the Kinect® camera only captures kinematics from the front of the camera to the front of the user.

By positioning the Kinect® camera at a height of 1.34 m above the floor with the appropriate mechanical camera angle adjustments and utilizing the Kinect® SDK software's inherent interpolation capability where less accuracy is required, the upper and lower body movements are captured providing a complete skeleton for rendering the onscreen avatar while allowing accurate and optimal data capture of the lower extremities.

From the code, it is possible to independently and simultaneously measure: the distance between the two feet relative to each other; the distance of the feet relative to a fixed point on the GPV floor; the distance of the two feet relative to the camera (in any direction on the XZ-plane, the YZ-plane or the XY-plane); the position of the feet over a particular point in the GPV; the height of the feet above the ground; the velocity of the feet in any direction or at any time captured by the Kinect®. These measurements are captured and stored in real-time and create the game play and the interactions of the real world movements with the VE as well as produce the performance metrics.

Figure 4:
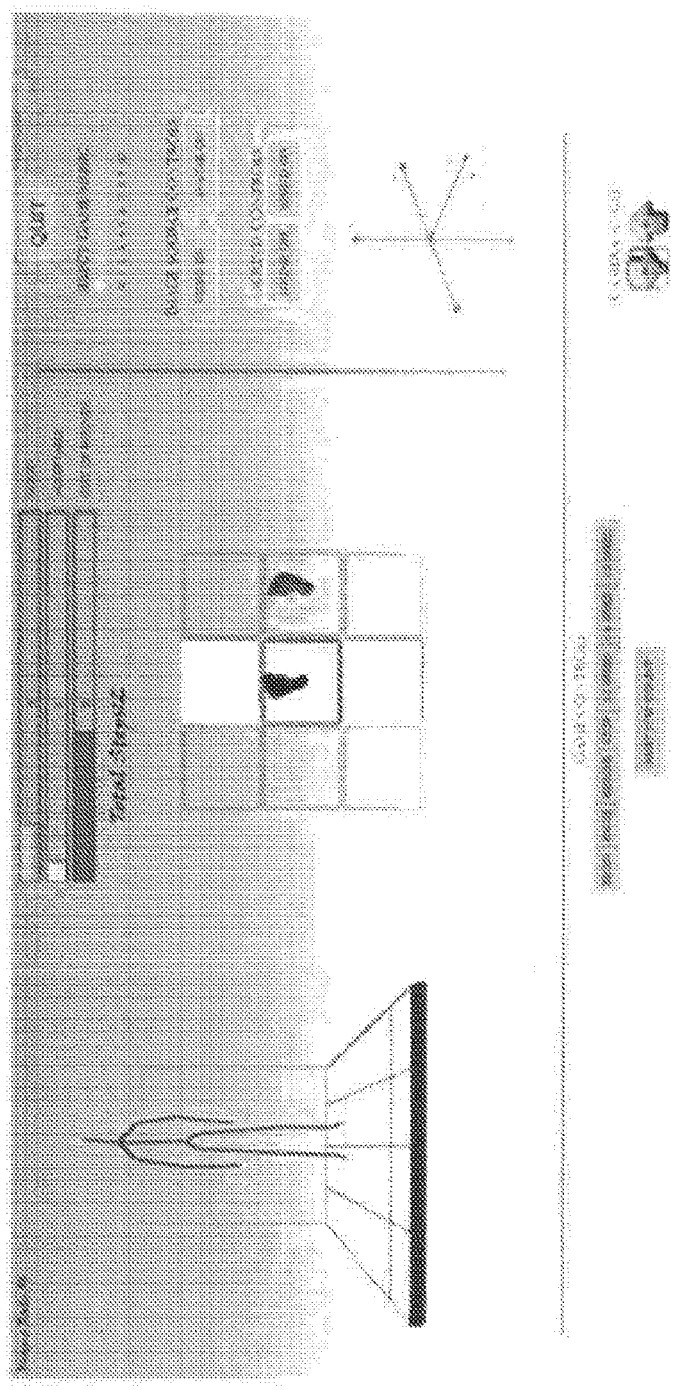
FIG. 4 is an illustration of a stepping set-up.

The stepping game was designed to address safety concerns and uses simple stepping actions that increase in stepping speed and complexity as the user's physical capability improves. This is enabled via various stepping and leg lifting sequences that respond to the user's stepping speed—they speed up or slow down as the user changes speed. The game also includes optional game sounds that augment information to the user about their stepping actions, as well as musical tracks that vary in tempo to aid in user engagement and pacing. The game also provides an option between an avatar and a video image of the user. On screen scores and graphs provide both the clinician and user feedback and engagement (see FIG. 4—shown with base skeleton avatar).

The game was also designed to collect temporal-spatial data, which are date/time stamped. The data collected are: the distance that a foot moves from a starting point yielding (a) stride length/step displacement of the user and/or (b) a positional metric for the return placement of the step; the speed that a foot moves relative to the Kinect® camera (as the fixed point) yielding an absolute reference point; the distance that a foot moves relative to the other foot; and/or steps (defined as Good, Acceptable and Out of Bounds) that are based on each user's level of accuracy providing specificity of feedback.

Validation of Kinematics

To validate the kinematics of Kinect®, it was compared with the Motus-Peak motion capture system, currently known as the Vicon®-Motus ("Vicon®"). The Kinect® camera was set up with the user centered 2.5 meters from the Kinect® camera and the Vicon® cameras approximately 2 meters from the user.

Data was collected from five healthy subjects—2 male, 3 females, ages 22-40 years. The data is presented below. However, additional data was also collected from 5 physical therapist clinicians and 5 persons post-stroke. Each participant was instrumented with reflective markers that were placed bilaterally on the first distal phalanx, calcaneus, lateral malleolus, fibular head, greater trochanter, anterior and posterior iliac spines. Participants then performed various steps with each leg: stepping forward; stepping backward; stepping right; and stepping left. The participants also raised each knee as high as possible. The calibration data was used to customize the game parameters for each subject.

Once the system was calibrated, participants performed the stepping patterns shown in Table I provided below. Actions 1 and 2 were performed six times per foot. Actions 3 and 4 were performed for 2 minutes each. All movements were captured simultaneously by both systems. In this document, data and analyses only for actions 1 and 2 are discussed.

TABLE 1

|   | Right Foot | Left Foot |
| --- | --- | --- |
| 1 | Step Right | Step Left |
| 2 | Step 45° to the Right | Step 45° to the Left |
| 3 | Kick a virtual ball, alternating the feet | |
| 4 | Execute a pre-programmed walking pattern | |

While the Kinect® only produces XYZ position data, the Vicon also produces velocity and acceleration data from the XYZ position data. For the purposes of the validation, only position and velocity data were processed from the Vicon®. The Vicon® position data was processed using the First Central Difference Method ("fCDM") shown as Mathematical Equation 1 below, and compared to the Vicon® velocity data to validate the chosen method of velocity calculation.

$$V = \frac{\partial x}{\partial t} \cong f'(t_i) \frac{f(t_i + h) - f(t_i - h)}{2h} \quad (1)$$

The fCDM was also applied to the Kinect® position data to calculate velocities. This ensured uniformity of the results across both systems and reduced error. All calculated velocities were plotted as absolute values to maintain uniformity with the Vicon® produced data. The Vicon® produces absolute values for velocity. All captured kinematic data were filtered in MATLAB 2014a using a 2nd order, two-way Butterworth Low-Pass Filter ("LPF") with a sample-rate of 200 Hz and a cut-off frequency of 15 Hz, resulting in a $4^{th}$ order Butterworth LPF.

The step distances (displacements) were measured as the difference between the start position (min) and the end position (max) and processed using the distance formula. The distance formula is expressed below as Mathematical Equation 2.

$$\text{Dist} = \sqrt{(x_2 - x_1)^2 + (y_2 - y_1)^2 + (z_2 - z_1)^2} \quad (2)$$

Since the Vicon® and Kinect® side stepping displacements were simple linear measures, they were mathematically processed to shift the plots to a zero baseline, and no other manipulations were applied. To calculate the 45° step displacements, the Kinect® kinematic data were mathematically processed using the simple Pythagorean for data in the X and Z planes. With respect to the Kinect® camera's orientation, the motion in the Y plane was negligible with respect to the XZ data. A scaling factor was used to scale the Kinect® measured step displacement to reflect the real world measure. The Vicon® produced a resultant value and no Pythagorean was needed to calculate the 45° step displacement. However, the data was mathematically processed to shift the plots to the X axis for a zero baseline. The Vicon® and Kinect® displacement and velocity data were validated using the Pearson Product-Moment Correlation Coefficient ("PPMCC"), and paired t-tests confirmed there were no differences between measurements. An alpha of 0.05 was set for all analyses.

Figures 5, 6:
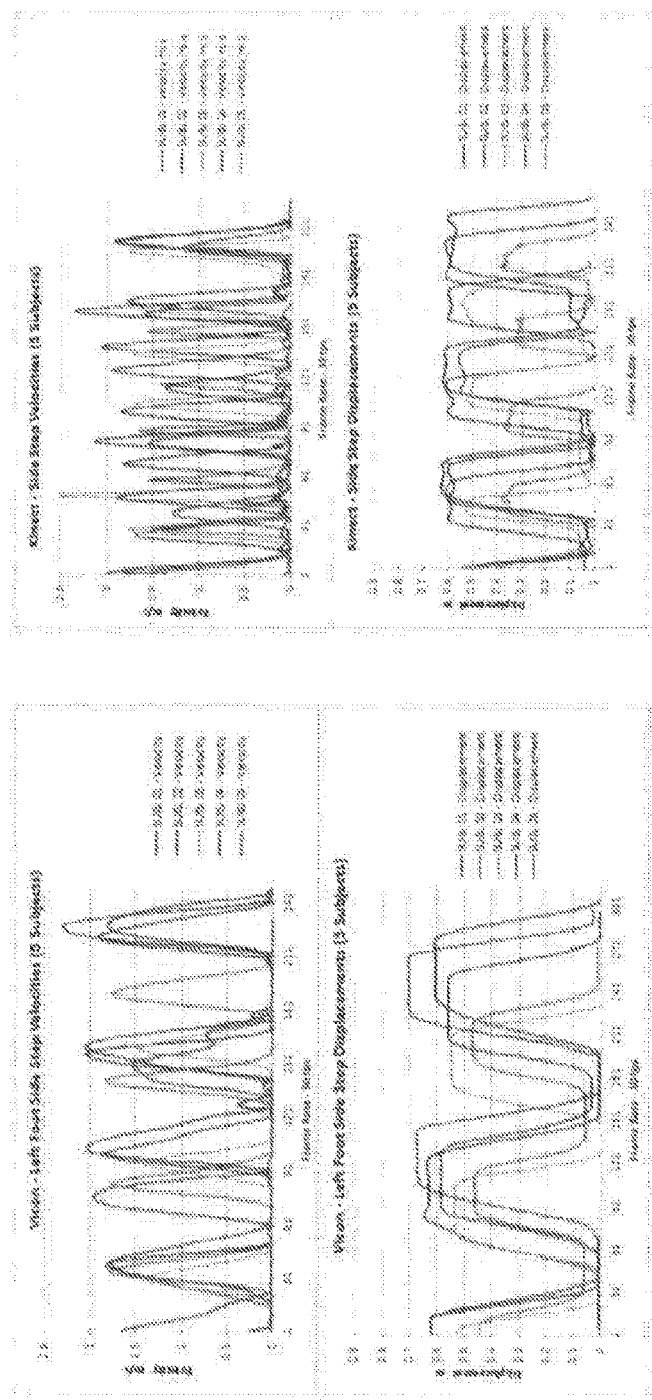
FIG. 5 is an illustration showing Vicon® left foot side step velocities (top) and displacements (bottom) plotted against a frame rate.
FIG. 6 is an illustration showing Kinect® left foot side step velocities (top) and displacements (bottom) plotted against a frame rate.
Figures 7, 8:
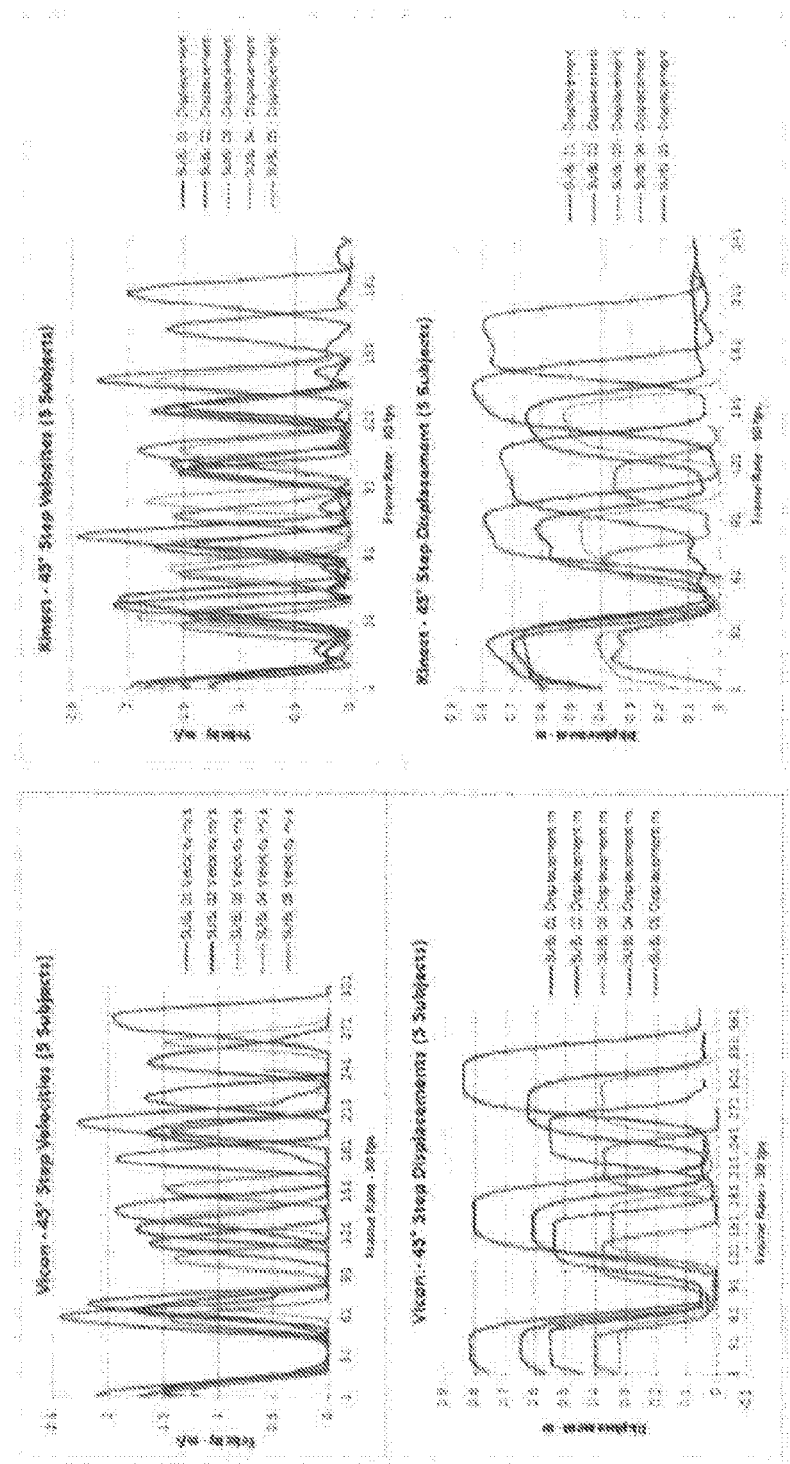
FIG. 7 is an illustration showing Vicon® and Kinect® left foot 45° step velocities (top) and displacements (bottom) plotted against a frame rate.
FIG. 8 is an illustration showing Kinect® left foot 45° step velocities (top) and displacements (bottom) plotted against a frame rate.

The resulting data for the five subjects is described below. Only three steps each for both the side step and 45° step are shown for clarity. PPMCC and t-test results are shown in TABLE 2. The Vicon® and Kinect® max/min and average step displacement values for the left foot side steps, and the corresponding max/min and average side step velocities (step out and step in motion) are shown in TABLE 3. The max/min and average step values for the left foot 45° steps, and the corresponding max/min and average 45° step velocities (step out and step in motion) are shown in TABLE 4. FIGS. 5 and 6 respectively show the Vicon® and Kinect® left foot side step velocities (top) and displacements (bottom) plotted against the frame rate. FIGS. 7 and 8 respectively show the Vicon® and Kinect® left foot 45° step velocities (top) and displacements (bottom) plotted against the frame rate.

TABLE 2

|  | Correlation | P-Value | t-test |
|---|---|---|---|
| Displacement | | | |
| Side Step | 0.890 | 0.043 | 0.541 |
| 45° Step | 0.992 | 0.001 | 0.607 |
| Velocity m/s | | | |
| Side Step: Step Out | 0.944 | 0.016 | 0.357 |
| Side Step: Step In | 0.868 | 0.057 | 0.746 |
| 45° Step: Step Out | 0.971 | 0.006 | 0.429 |
| 45° Step: Step In | 0.929 | 0.023 | 0.658 |

TABLE 3

| | | Side Step Distance in Meters | | | | | | Side Step Velocity in m/s | | | |
|---|---|---|---|---|---|---|---|---|---|---|---|
| | | Kinect® | | | Vicon® | | | Kinect® | | Vicon® | |
| | Step | MAX | MIN | DIFF | MAX | MIN | DIFF | OUT | IN | OUT | IN |
| SUBJ 01 | 1 | 0.59 | 0.00 | 0.59 | 0.59 | 0.00 | 0.59 | 1.66 | 1.82 | 1.82 | 1.85 |
| | 2 | 0.61 | 0.00 | 0.61 | 0.56 | 0.00 | 0.56 | 1.84 | 2.05 | 2.02 | 1.90 |
| | 3 | 0.58 | 0.00 | 0.58 | 0.60 | 0.00 | 0.60 | 1.77 | 1.92 | 1.61 | 1.77 |
| | Avg. | 0.59 | 0.00 | 0.59 | 0.58 | 0.00 | 0.58 | 1.76 | 1.93 | 1.82 | 1.84 |
| SUBJ 02 | 1 | 0.63 | 0.00 | 0.63 | 0.62 | 0.00 | 0.62 | 1.78 | 1.97 | 1.82 | 1.96 |
| | 2 | 0.64 | 0.00 | 0.64 | 0.63 | 0.00 | 0.63 | 1.58 | 1.95 | 1.54 | 1.78 |
| | 3 | 0.64 | 0.00 | 0.64 | 0.61 | 0.00 | 0.61 | 1.59 | 1.74 | 1.45 | 1.77 |
| | Avg. | 0.64 | 0.00 | 0.64 | 0.62 | 0.00 | 0.62 | 1.65 | 1.89 | 1.60 | 1.84 |
| SUBJ 03 | 1 | 0.53 | 0.00 | 0.53 | 0.52 | 0.00 | 0.52 | 1.82 | 1.91 | 2.02 | 2.18 |
| | 2 | 0.53 | 0.00 | 0.53 | 0.53 | 0.00 | 0.53 | 1.78 | 2.09 | 1.97 | 2.22 |
| | 3 | 0.57 | 0.00 | 0.57 | 0.55 | 0.00 | 0.55 | 2.21 | 2.15 | 1.87 | 2.20 |
| | Avg. | 0.54 | 0.00 | 0.54 | 0.53 | 0.00 | 0.53 | 1.94 | 2.05 | 1.95 | 2.20 |
| SUBJ 04 | 1 | 0.54 | 0.00 | 0.54 | 0.67 | 0.00 | 0.67 | 1.99 | 1.89 | 1.78 | 2.08 |
| | 2 | 0.59 | 0.00 | 0.59 | 0.71 | 0.00 | 0.71 | 2.11 | 1.95 | 2.06 | 2.31 |
| | 3 | 0.61 | 0.00 | 0.61 | 0.69 | 0.00 | 0.69 | 2.32 | 1.90 | 2.08 | 2.34 |
| | Avg. | 0.58 | 0.00 | 0.58 | 0.69 | 0.00 | 0.69 | 2.14 | 1.91 | 1.97 | 2.24 |
| SUBJ 05 | 1 | 0.38 | 0.00 | 0.38 | 0.40 | 0.00 | 0.40 | 1.34 | 1.83 | 1.47 | 1.44 |
| | 2 | 0.36 | 0.00 | 0.36 | 0.37 | 0.00 | 0.37 | 1.47 | 1.57 | 1.40 | 1.47 |
| | 3 | 0.36 | 0.00 | 0.36 | 0.37 | 0.00 | 0.37 | 1.60 | 1.43 | 1.40 | 1.38 |
| | Avg. | 0.37 | 0.00 | 0.37 | 0.38 | 0.00 | 0.38 | 1.47 | 1.61 | 1.42 | 1.43 |

TABLE 4

| | | 45° Step Distance in Meters | | | | | | 45° Step Distance in m/s | | | |
| | | Kinect® | | | Vicon® | | | Kinect® | | Vicon® | |
| | Step | MAX | MIN | DIFF | MAX | MIN | DIFF | OUT | IN | OUT | IN |
|---|---|---|---|---|---|---|---|---|---|---|---|
| SUBJ 01 | 1 | 0.78 | 0.00 | 0.82 | 0.82 | 0.00 | 0.82 | 1.96 | 2.08 | 1.93 | 2.08 |
| | 2 | 0.79 | 0.00 | 0.80 | 0.80 | 0.00 | 0.80 | 2.45 | 1.91 | 2.42 | 1.93 |
| | 3 | 0.83 | 0.00 | 0.84 | 0.84 | 0.00 | 0.84 | 2.27 | 2.01 | 2.22 | 1.94 |
| | Avg. | 0.82 | 0.00 | 0.82 | 0.82 | 0.00 | 0.82 | 2.23 | 2.00 | 2.19 | 1.98 |
| SUBJ 02 | 1 | 0.61 | 0.00 | 0.61 | 0.64 | 0.00 | 0.64 | 1.84 | 2.13 | 1.71 | 2.15 |
| | 2 | 0.57 | 0.00 | 0.57 | 0.61 | 0.00 | 0.61 | 1.76 | 1.63 | 1.72 | 1.64 |
| | 3 | 0.62 | 0.00 | 0.62 | 0.62 | 0.00 | 0.62 | 1.80 | 1.66 | 1.64 | 1.76 |
| | Avg. | 0.60 | 0.00 | 0.60 | 0.62 | 0.00 | 0.62 | 1.80 | 1.81 | 1.69 | 1.85 |
| SUBJ 03 | 1 | 0.38 | 0.00 | 0.38 | 0.32 | 0.00 | 0.32 | 1.24 | 1.26 | 1.27 | 1.27 |
| | 2 | 0.38 | 0.00 | 0.38 | 0.35 | 0.00 | 0.35 | 1.46 | 1.41 | 1.48 | 1.47 |
| | 3 | 0.41 | 0.00 | 0.41 | 0.38 | 0.00 | 0.38 | 1.54 | 1.54 | 1.57 | 1.51 |
| | Avg. | 0.39 | 0.00 | 0.39 | 0.35 | 0.00 | 0.35 | 1.41 | 1.40 | 1.44 | 1.42 |
| SUBJ 04 | 1 | 0.56 | 0.00 | 0.56 | 0.55 | 0.00 | 0.55 | 1.43 | 1.82 | 1.52 | 1.84 |
| | 2 | 0.56 | 0.00 | 0.56 | 0.53 | 0.00 | 0.53 | 1.71 | 1.92 | 1.71 | 1.97 |
| | 3 | 0.56 | 0.00 | 0.56 | 0.55 | 0.00 | 0.55 | 1.64 | 1.85 | 1.74 | 1.92 |
| | Avg. | 0.56 | 0.00 | 0.56 | 0.54 | 0.00 | 0.54 | 1.59 | 1.86 | 1.66 | 1.91 |
| SUBJ 05 | 1 | 0.35 | 0.00 | 0.35 | 0.40 | 0.00 | 0.40 | 1.55 | 1.43 | 1.47 | 1.44 |
| | 2 | 0.39 | 0.00 | 0.39 | 0.37 | 0.00 | 0.37 | 1.50 | 1.94 | 1.40 | 1.47 |
| | 3 | 0.36 | 0.00 | 0.36 | 0.37 | 0.00 | 0.37 | 1.53 | 1.53 | 1.40 | 1.38 |
| | Avg. | 0.37 | 0.00 | 0.37 | 0.38 | 0.00 | 0.38 | 1.53 | 1.63 | 1.42 | 1.43 |

The stepping game(s) described herein was(were) found to be an acceptable form of balance training. The correlations between the Vicon® and Kinect® cameras were greater than r=0.9 across all the movements measured indicating strong relationship between the systems. T-tests confirmed there was no difference in the measurements.

Initial laboratory testing indicated a high correlation between the displacement and velocity measurements captured by the Kinect® and as compared to the Vicon®. The graphical representation of the displacement may indicate a slight variations in velocities and step displacements between the Kinect® and the Vicon® values. However, these variations can easily be corrected using scaling factors. The Kinect® and the Camera system described herein readily captures all the necessary data to describe the lower limb movement and velocity.

From the technology design and testing and the technology validation sessions, the findings are summarized as follows.
1. A useable physical space that allows the user to move about unhindered and perform tasks/play games in the virtual world created by our software. This volume measures 20 m³ at a distance of 1.5 m from the Kinect® camera, with the Kinect® camera placed 1.34 m above the floor.
2. Comparable data were captured by Kinect® with the Vicon® motion capture system for movements used in the games capture system.
3. A method of calculating velocities with the first Central Difference Method by comparing it to the velocities measured by the Vicon® and applying the derivative to the displacements captured by the Vicon® was supported.
4. The Kinect® captured a reasonably accurate measurement of the stepping displacements and velocities.
Overall, a motion capture system was designed with a useable game-play volume. The motion capture system's ability to capture accurate motion data was validated. A useable set of data for a game was generated to promote mobility and balance in adults by using stepping.

Exemplary Methods

Figure 9:
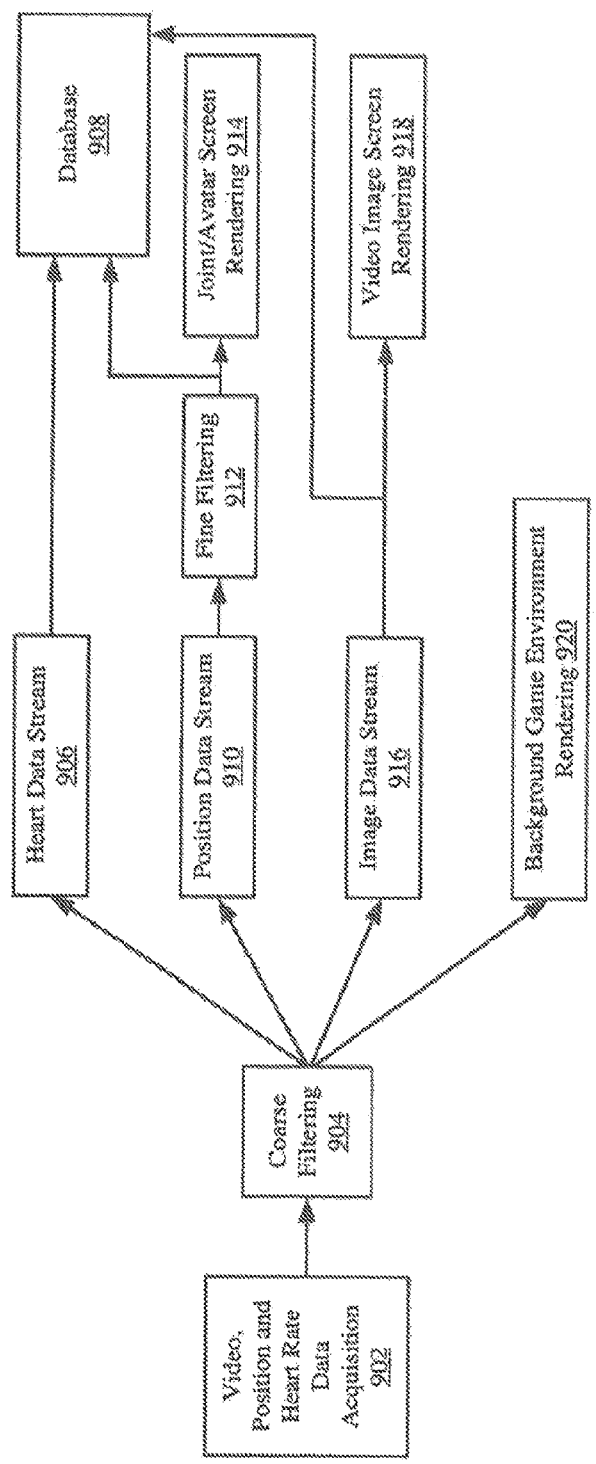
FIG. 9 is an illustration that is useful for understanding an exemplary technique for providing a DHP game.

Referring now to FIG. 9, there is provided an illustration that is useful for understanding an exemplary technique for providing a DHP game 108 of FIG. 1). The DHP game can include, but is not limited to, an MDBMF game. In some scenarios, the DHP game has the capability to measure performance on balance and coordination tasks. These are standardized tasks that have normative data associated with them. The standardized tasks are implemented by collection of motion that allows for concurrent measurement and testing, resulting in data to interpret and track performance. The current tests include a Four Square Step Test ("FSST") and a Single Limb Stance ("SLS") test. The FSST is a test of bilateral lower extremity coordination and balance. The SLS test is a test of balance. Other assessments/tests may also be implemented via the DHP game. These assessments/tests which are implemented by the DHP game are selected in accordance with a particular application.

Figure 11:
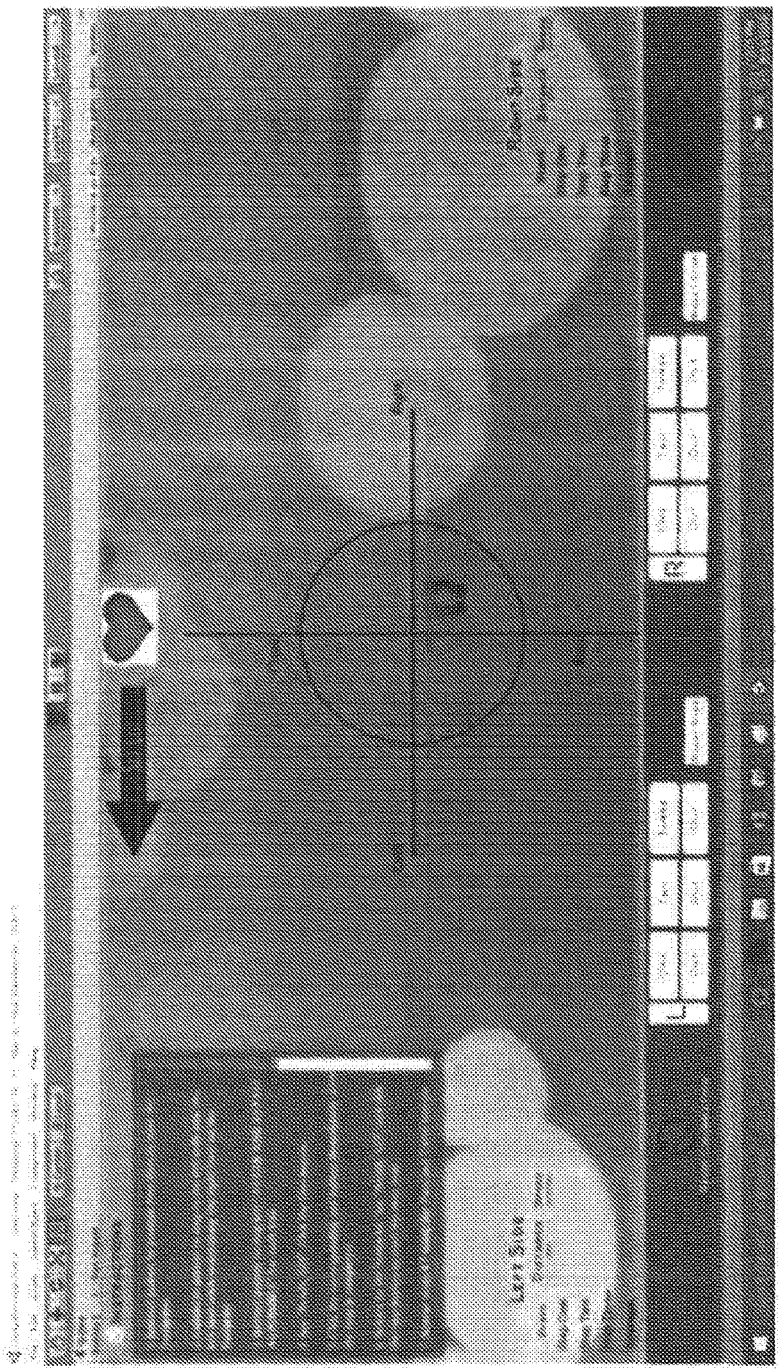
FIG. 11 is an illustration of an exemplary Graphical User Interface ("GUI") of a DHP game.

The DHP game can be calibrated based on the user's ability. The calibration is for stepping distance, stepping rate and/or stepping height. These three (3) actions are the building blocks for the DHP game play volume and presentation of the targets (explained below) which are adjusted to the person's ability. A procedure to calibrate side step, forward and backward step, and height for both lower extremities independently is implemented in the DHP game. This is evident from the GUI illustrated in FIG. 11.

Figure 12:
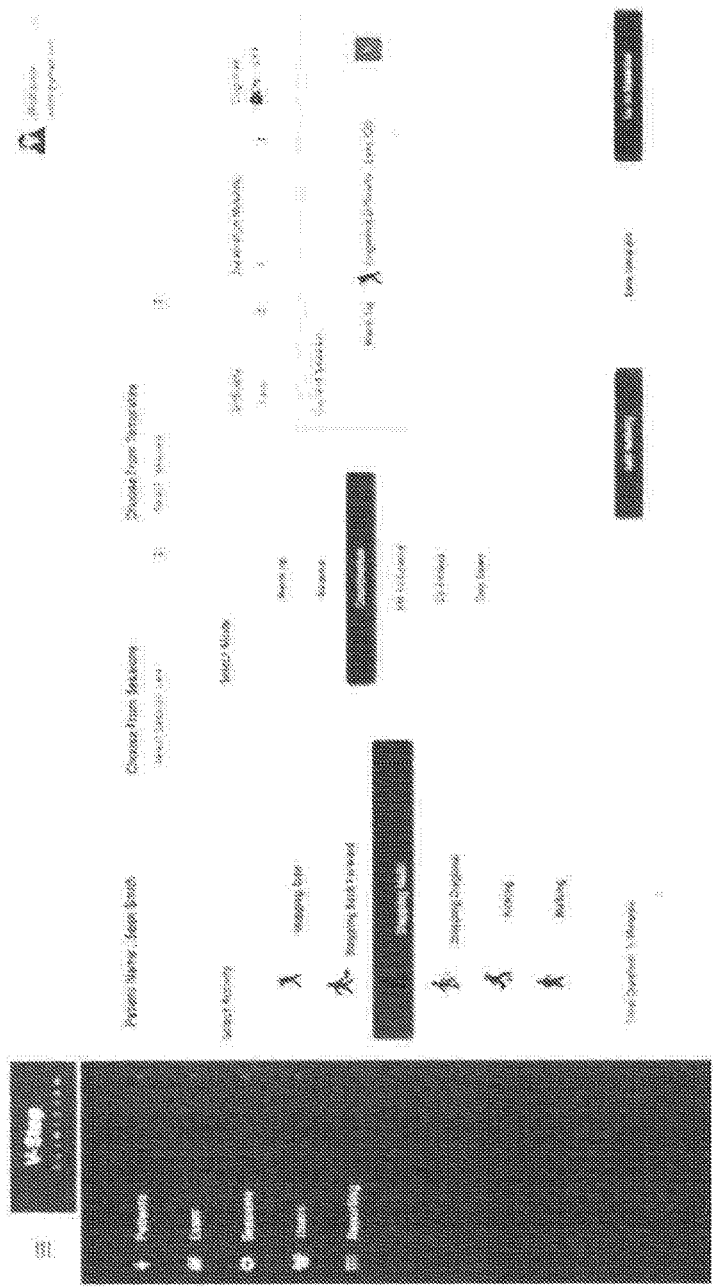
FIG. 12 is an illustration of a GUI for planning a session.
Figure 13:
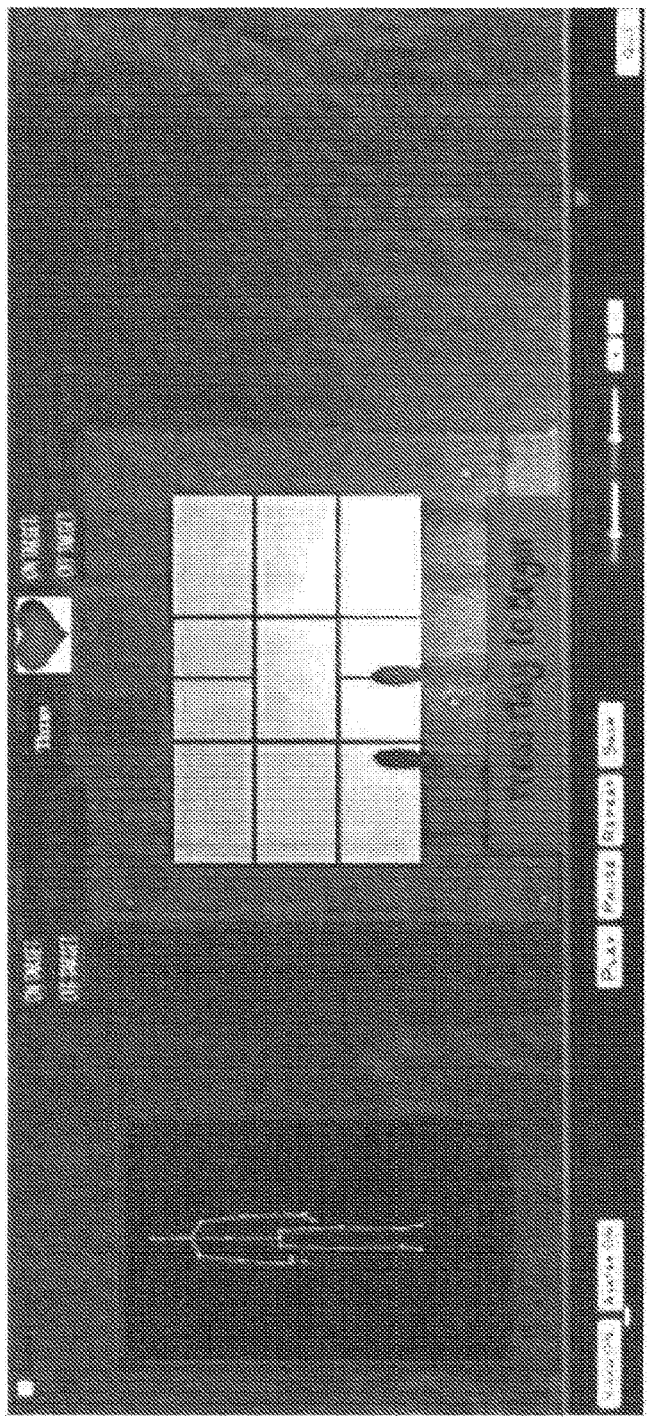
FIG. 13 is an illustration of a stepping set-up GUI.

Additionally, a high degree of customization is afforded to a clinician in configuring the DHP game based tasks, modes of play, difficulty, duration and cognitive load. An exemplary GUI facilitating such customization is provided in FIG. 12. What differentiates the DHP game from other conventional video games for rehabilitation is that the DHP game is task based as opposed to exercise based. The tasks of the DHP game are referred to as mini games for fundamental movement mobility. The mini games can include, but are not limited to, the following: side step; back and forward step; multi-step; diagonal step; kicking; and walking. In addition to the tasks, the clinician can select the mode that the tasks should emphasize. The modes are used to design an exercise session by including warm up and cool down. The modes are customizable for addressing the relevant impairments of the patient (e.g., balance, coordination, cardiovascular fitness, neuromuscular endurance). One exemplary mode comprises a self-paced mode. This feature is especially helpful when the clinician wants to orient the patient to the mini games and not spend time constructing a highly customized session. To complete the game parameters, the clinician can specify cognitive difficulty and duration. Finally, the addition of cognitive tasks concurrent with a movement task facilitates skill training in the DHP game that is most likely to transfer to real work improvements. Using these building blocks, the clinician is able to create a session, modify the session and save the session for future use.

Once the session is configured, the mini games are played in the rehabilitation game GUI. The multi-step, kicking and walking games are self-paced as well as game-paced. All the other games are game paced. Within the rehabilitation game GUI, real time adjustments of the game difficulty can be made by manipulating distance and speed parameters. There is visualization as well for the user and the respective avatar. These tools can be used for posture and movement re-education.

As shown in FIG. 9, the present solution begins with the acquisition of video, position and heart rate data as a person interacts with a computing device (e.g., computing device 106 of FIG. 1) executing the DHP game, as shown by functional block 902. The user-computer interaction can include, but is not limited to, copying movements of an avatar, playing a goal-directed video game, and/or interacting with virtual objects and events in a meaningful way.

In those or other scenarios, the video, position information and heart rate data are obtained using a depth camera (e.g., depth camera 102 of FIG. 1). The position data can be expressed in an xyz coordinate system and a temporal system (e.g., a $\frac{1}{60}^{th}$ per second frames of position data). Depth cameras are well known in the art, and therefore will not be described herein. In some scenarios, the depth camera is a Commercial Off The Shelf ("COTS") camera such as a Kinect® camera. The Kinect® camera generally emits infrared signals (or dots); and creates an outline of a person's shape. From the outline, a person's joints and body segments can be recreated. This allows the person's movements to be tracked, measured and represented in a VE.

In some scenarios, the heart rate data is acquired using infrared technology of the depth camera, as opposed to or in addition to RGB spectrum based technology of the depth camera. In this regard, it should be understood that a person's skin color is not a factor in determining the person's body temperature when using infrared technology, but is when using RGB spectrum based technology. This feature of the RGB spectrum based technology has significant disadvantages in particular scenarios since a person with a lighter complexion experiences a greater degree of variation from light-to-pink-to-red as compared to a person with a darker complexion. In effect, standardization of a technique for acquiring temperatures of a plurality of people having different complexions using only RGB spectrum based technology is not achievable to a satisfactory level. As such, infrared technology is employed herein in addition to or as an alternative to RGB spectrum based technology.

Depending on how much exertion the person has performed, his(her) body temperature will rise above the typical 98° F. This temperature rise is captured on the forehead, checks and/or jaw line of the person regardless of skin color using the infrared technology. An exemplary manner in which this temperature capturing is achieved in some scenarios will now be described in relation to FIG. 10. Still, it should be understood that an infrared sensor along with a body mapper can be used to locate and identify individual users and their faces in front of the camera. Data is captured from the infrared and camera stream within the tracked face. The data from this stream is used to calculate the variation of density between adjacent pixels. The change in the pixel density of the infrared stream is analyzed along with change in color within the pixels over time. The results of this analysis is used to determine the heart rate variability. The heart rate variability can be displayed as a pulse on the GUI of the DHP game.

Figure 10:
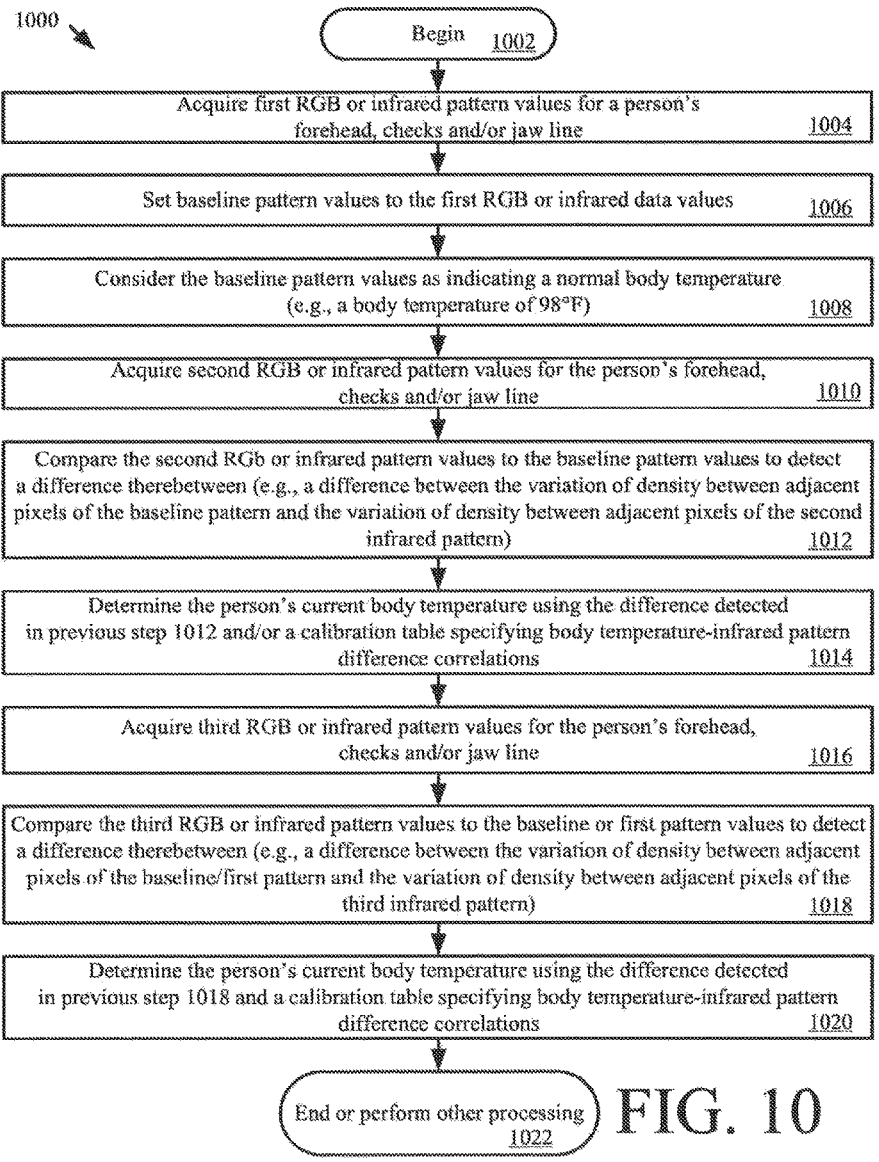
FIG. 10 is an illustration of a flow diagram for an exemplary method for determining a person's body temperature using infrared technology of a depth camera.

Referring now to FIG. 10, there is shown a flow diagram of an exemplary method 1000 for determining a person's current heart rate based on either RGB sensor data, infrared sensor data or a combination of both. Method 1000 begins with step 1002 and continues with step 1004 where first RGB or infrared pattern values are acquired for a person's forehead, checks and/or jaw line. The first RGB or infrared pattern values are used as baseline pattern values as shown by step 1006. The base line pattern values are considered in step 1008 as indicating a normal body temperature (e.g., 98° F.).

In a next step 1010, second RGB or infrared pattern values are acquired for the person's forehead, checks and/or jaw line. The second infrared pattern values are compared in step 1012 to the base line pattern values to detect a difference therebetween. The person's current body temperature is then determined in step 1014 using at least the difference detected in step 1012. Step 1012 can involve determining a difference between the variation of density between adjacent pixels of the baseline infrared pattern and the variation of density between adjacent pixels of the second infrared pattern.

In some scenarios, a calibration table is provided that specifies body temperature-infrared pattern difference correlations. The calibration table is generated based on the following fundamental principles. The RGB and IR data streams enable the program to calculate the changes in color brightness at thirty (30) frames per second (60 Hz). Changes in color density/IR radiation correlates to the contraction of the heart—systole. Essentially, the face is darker/hotter on systole compared to diastole. The IR and RGB values will change slightly over time as the heart contracts and relaxes. This frequency correlates to heart frequency (heart rate). The pulse is found by performing a coarse and fine filtering algorithm to pass only the frequency band corresponding to heart rate and rejecting noise signals.

Referring again to FIG. 10, method 1000 continues with step 1016 where third RGB or infrared pattern values are acquired for the person's forehead, checks and/or jaw line. The third RGB or infrared pattern values are then compared in step 1018 to the baseline or first pattern values to detect a difference therebetween. The person's current body temperature is then once again determined using at least this difference in infrared pattern values. The above TABLE may also be employed in step 1020 for determining the person's current body temperature. Subsequent to completing step 1020, step 1022 is performed where method 1000 ends or other processing is performed.

The present solution is not limited to the method 1000 described in FIG. 10. Another exemplary method 1500 is provided in FIG. 15. Notably, steps of both methods may be combined so as to provide yet another method. For example, although not shown in FIG. 10, method 1000 involves the performance of at least steps 1504 and 1506 of FIG. 15 as would be understood by a person skilled in the art.

Generally, the Kinect sensor provides multiple streams of data. In order to enable heart rate calculations, a high definition camera stream (RGB data) and an IR stream is employed along with face tracking. An IR data stream returns data as a number representing the intensity of a specific pixel, a number that varies between 0 and 65,536.

For every iteration of the IR source beams, the camera captures the reflection and a number is returned (e.g., 30 fps). Using the face tracking code, the pixels that determine the area of the face are defined. Data from the pixels within this area is captured over time for every pixel.

Using Individual Component Analysis ("ICA") algorithms on RGB data streams and IR data streams, the individual separation of the components is analyzed to obtain a pulse. When heart pumps blood to the face, more light is absorbed by the skin. The camera picks up the skin darkening. The intensity of the skin varies in a periodic manner corresponding to the contraction and relaxation of the heart. This change in frequency over time will correspond to the pulse. Further filtering is done to remove other signals and provide a clean signal that can be represented as the heart rate.

Figure 15:
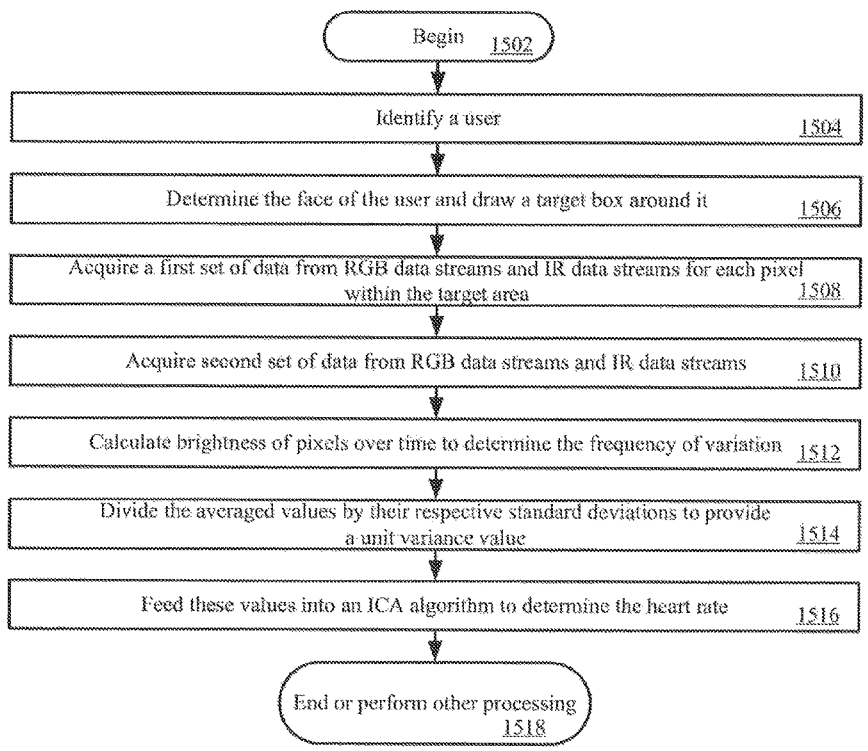
FIG. 15 is a flow diagram of an exemplary method for determining a user's heart rate.

As shown in FIG. 15, method 1500 begins with step 1502 and continues with step 1504 where a user is identified. In a next step 1506, the face of the user is determined. A target box is then drawn around the user's face. A first set of data is acquired from RGB data streams and IR data streams are acquired in step 1508 for each pixel in the target area. A second set of data is acquired from the RGB data streams and IR data streams, as shown by step 1510. Subsequently, step 1512 is performed where computations are performed. Specifically the brightness of pixels are calculated over time to determine the frequency of variation. The averaged values are then divided by their respective standard deviations to provide a unit variance value, as shown by step 1514. These values are fed into an ICA algorithm to determine the heart rate, as shown by step 1516. After completing step 1516, method 1500 ends or other processing is performed in step 1518.

ICA algorithms are well known in the art, and therefore will not be described in detail herein. Still, it should be understood that in some scenarios the ICA algorithm involves performing the following operations for blind source separation: generating a matrix S containing the signal from four data streams (RGB and IR data); assigning a two by two matrix; generating the observed (mixed) signals; performing a linear transformation of the data to remove any correlations; performing a fast Fourier to obtain the signals in frequency domain; filtering the resulting data to obtain a clean signal; and calculating the heart rate from the resultants.

The present invention is not limited to the ICA algorithms. For example, K-means algorithms, back propagation or feedforward artificial neural-network algorithms or any other algorithms providing predictive analysis can be used herein for determining a person's heart rate using RGB and/or IR data.

Exemplary code for initializing sensors (e.g., motion sensors 104 of FIG. 1) and Kinect® camera for data acquisition is provided below.

```
//initialize the sensor and capture video data. This is filtered coarsely
as described below
private void InitializeKinectSensor(KinectSensor kinectSensor)
{
    if (kinectSensor != null)
    {
        ColorImageStream colorStream =
        kinectSensor.ColorStream;
        colorStream.Enable( );
        this._ColorImageBitmap = new
        WriteableBitmap(colorStream.FrameWidth,
            colorStream.FrameHeight, 96, 96,
            PixelFormats.Bgr32, null);
```

-continued

```
        this._ColorImageBitmapRect = new Int32Rect(0, 0,
        colorStreamFrameWidth,
            colorStream.FrameHeight);
        this._ColorImageStride = colorStream.FrameWidth *
            colorStream.FrameBytesPerPixel;
        if (color == 1)
        {
        }
}
```

Referring again to FIG. 9, a next functional block 904 is shown for coarse filtering operations. The coarse filtering operations are performed using some or all of the data acquired in functional block 902 using the depth camera. For example, as shown in FIG. 9, the coarse filtering is applied to the heart rate data, position data and/or video data. The coarse filtering generally maintains a fixed frame rate (e.g., $\frac{1}{60}^{th}$ of a second) so that the data streaming is constant. Notably, the coarse filtering may not be applied to the heart rate data. In this case, the heart rate data would simply bypass the coarse filtering operations.

The coarse filtering is generally performed to address rough skeletal movements of the avatar (i.e., a displayed figure representing a particular person (e.g., the user of system 100 of FIG. 1) in the DHP game) by removing data associated with any extraneous signals resulting from light and/or slow/slight movements of the person. The rough movements of the avatar may be caused by the person's behavior (e.g., shaky behavior), sensor noise and/or clothing. The variance of the person's joint position can negatively affect the DHP game so as to create an awkward and/or displeasing user experience. The coarse filtering provides a means to normalize position values by reducing the variance in joint positions from frame to frame. In this regard, the coarse filtering is controlled via the following five (5) smoothing parameters: correction; prediction; jitter radius (value within which the filtered and unfiltered data should fall under); double exponential smoothing (factor used to remove high frequency noise); and maximum deviation (maximum allowed range deviation from raw data). Operations implementing the five (5) listed smoothing parameters facilitate the adjustment of joint position values calculated in each frame according to the desired smoothing behavior.

In some scenarios, the correction operation involves taking a float ranging from zero (0) to one (1.0). The lower the number, the more correction is applied. The prediction operation involves returning the number of frames predicted.

The jitter radius operation involves clamping on frame-over-frame variations in the person's lower extremity positions. The clamping is achieved by: comparing a raw unfiltered position value to a filtered position value that was calculated for the previous frame; determining if a difference between the two position values exceeds a jitter radius; and clamping the raw unfiltered position value to the jitter radius if the difference is determined to exceed the jitter radius. The jitter radius operation is performed prior to when the raw unfiltered position data is input into the double exponential smoothing operations.

The maximum deviation operation is performed to define the maximum radius in meters that the filtered positions are allowed to deviate from the raw data. In this regard, the maximum deviation operation generally involves clamping filtered position values that are more than the maximum radius from the raw data. This is achieved by: comparing a filtered position value with the unfiltered position value for the same frame; determining if a difference between the two position values exceeds a max deviation radius; and clamping the filtered position value to a max deviation radius when it is determined that the difference exceeds the max deviation radius. The maximum deviation operation is performed after the double exponential smoothing operations.

The double exponential smoothing operations involve producing a smoothed time series of the person's lower extremity position data by removing high frequency noise. Techniques for double exponential smoothing are well known in the art. Any known or to be known double exponential smoothing technique can be used herein without limitation. For example, in some scenarios a Holt's double exponential smoothing algorithm is employed.

Exemplary code for implementing the coarse filtering operations is provided below.

on accurate movement patterns. In order to capture accurate positional data when the position is standing still, moving forwards or moving backwards, any high frequency data acquired during the movement itself (i.e., as the person transitions from standing, stepping and landing) needs to be removed. Accordingly, the fine filter looks at any deviation in the person's movement, a predicted value based on prior movements by the person, and a bandwidth how far the person can deviate in their movements to identify any data that does not reflect the person's typical movement (e.g., data associated with captured movements of other objects/persons in a surrounding environment, light changes in a surrounding environment and/or shadows occurring in a surrounding environment). This identified data is then removed from the acquired data so as to obtain data specifying more precise and localized patterns of the person.

```
//Coarse filtering
kinectSensor.SkeletonStream.Enable(new TransformSmoothParameters( )
{
    Correction = 0.5f,
    JitterRadius = 0.07f,
    MaxDeviationRadius = 0.04f,
    Smoothing = 0.5f
});
kinectSensor.SkeletonFrameReady += Kinect_SkeletonFrameReady;
kinectSensor.ColorFrameReady += Kinect_ColorFrameReady;
kinectSensor.Start( );
this.FrameSkeletons = new Skeleton[this.Kinect.SkeletonStream.FrameSkeletonArrayLength];
    }
}
private void Kinect_ColorFrameReady(object sender, ColorImageFrameReadyEventArgs e)
{
    GetCurrentFrameRate( );
    //CenterStance( );
    FrameRate.Content = "Frame Rate " + (int)(currentFrameRate);
    using (ColorImageFrame frame = e.OpenColorImageFrame( ))
    {
        if (frame != null)
        {
            byte[ ] pixelData = new byte[frame.PixelDataLength];
            frame.CopyPixelDataTo(pixelData);
            this._ColorImageBitmap.WritePixels(this._ColorImageBitmapRect, pixelData,
                this._ColorImageStride, 0);
        }
    }
}
```

The present solution is not limited to the above exemplary code. The coarse filtering can be implemented in accordance with a particular application and in any software language format.

Upon completing the coarse filtering, the data is recorded to a database as shown by functional blocks 906 and 908. The position data is also optionally passed to a fine filter as shown by functional blocks 910 and 912. The image data is used to generate a video image screen rendering as shown by functional blocks 916 and 918. All or some of the data is also used to render a background game environment as shown by functional block 920.

The fine filtering is performed to stop the avatar from flickering on the display screen as a result of lighting conditions (e.g., low light conditions). The fine filtering uses the same parameters as the coarse filtering, but with different constant values therefore. The fine filtering may be continuously performed, periodically performed or selectively performed when the lighting is poor making the data stream less consistent.

The fine filtering is applied only to the position data indicating body movements because it is desirable to hone in In some scenarios, the fine filtering involves smoothing, error detection, prediction, maximum deviation and jitter radius operations. The smoothing regulates how the value is corrected—a relatively high smoothing value decreases responsiveness/increases latency while a lower smoothing value corrects more slowly and appears smoother. Exemplary code for implementing the fine filtering operations is provided below.

```
//Second filtering to fine filter as described below
private void Kinect_SkeletonFrameReady(object sender,
SkeletonFrameReadyEventArgs e)
{
    // Smoothed with some latency.
    // Filters out medium jitters.
    TransformSmoothParameters smoothingParam = new
    TransformSmoothParameters( );
    {
        // Increased smoothing value = decreased
        responsiveness/increased latency.
        smoothingParam.Smoothing = 0.2f;
        // Higher value corrects toward the raw data more quickly,
        // Lower value corrects more slowly and appears smoother.
```

```
    smoothingParam.Correction = 0.6f;
    // No. of frames to predict into the future.
    smoothingParam.Prediction = 0.5f;
    // Determines how aggressively to remove jitter from the
    raw data.
    smoothingParam.JitterRadius = 0.3f;
    // Max radius (in meters) that filtered positions can deviate
    from raw data.
    smoothingParamMaxDeviationRadius = 0.1f;
};
```

Notably, the exemplary code provided above was written using the Microsoft Kinect® Software Development Kit ("SDK") to allow for both a coarse and fine filtering that yields high quality data for the lower extremities of a person. The filtering functions are smoothing, error detection, predication, deviation maximum and jitter radius. This allows the collection of data under low light conditions, which represent precise motion/movement patterns of the user.

Figure 14:
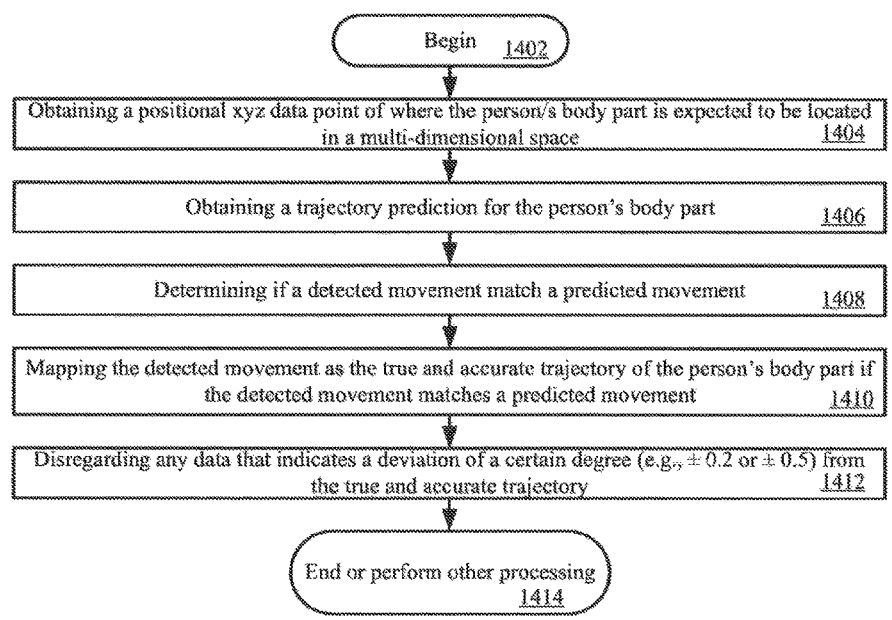
FIG. 14 is a flow diagram of an exemplary method for processing data.

In low light conditions, the camera needs light reflected off of the person in order to detect movements thereof. Reflected light depends on the type and drape of the fabrics being worn by the person and/or covering adjacent objects. The software (e.g., gaming software 224 of FIG. 2) employed herein is designed to discern between (a) a person's body part and an object in low light conditions and (b) a moving object/person and a stationary object/person based on the detected reflect light conditions regardless of the type and drape of the fabrics being worn by the person and/or covering adjacent objects. In this regard, the software is operative to perform the following operations as shown by steps 1402-1414 of FIG. 14: obtaining a positional xyz data point of where the person's body part is expected to be located in a multi-dimensional space; obtaining a trajectory prediction for the person's body part; determining if a detected movement match a predicted movement; mapping the detected movement as the true and accurate trajectory of the person's body part if the detected movement matches a predicted movement; and disregarding any data that indicates a deviation of a certain degree (e.g., ±0.2 or ±0.5) from the true and accurate trajectory. These operations are implemented at least partially by the coarse and fine filtering operations.

Temporal spatial parameters of the lower extremity are output. The body has a time frame reference and a space frame reference. The space frame reference is the xyz coordinates to the camera and other objects. The time frame reference is the time at which data is acquired. The time frame reference allows the software to determine (with a high degree of accuracy) whether a person's movement is forwards, backwards, to the right or to the left by referencing data associated with previous frames. Each frame is marked at $\frac{1}{60}^{th}$ of a second. The relative position of the person's ankle to knee, the knee to a toe, the toe to the ankle can be tracked over time using the temporal spatial information. Accordingly, the software is able to determine if the person's movement is normal or abnormal (e.g., the foot was curved instead of straight or the hip swung out or rotated at times when it should not have) based on the tracked lower body part's relative positions. This information can be used by the software to diagnose a medical condition (e.g., paralysis or underlying medical condition) and/or dynamically generate a treatment plan for the person. The treatment plan is then used to dynamically modify the game in real time such that it is customized for facilitating the treatment of the person's particular medical condition. Consequently, future iterations of the game facilitate diagnostic testing. In the present solution, the data is collected and used with evidence based therapeutic activities embedded in a virtual environment that has game features.

The analysis of a person's lower extremities is in contrast to what other companies who consider movement of the person's entire body. In this regard, it should be understood that the present solution is able to identify whether the lower limb motion is normal or abnormal. In conventional systems, this ability does not exist because acquired data specifying total body movement does not have the requisite granularity required for identifying normal and/or abnormal lower limb movements. Consequently, these conventional systems cannot be used to provide diagnostic testing of a person's natural gate or other low extremity movements.

Immediate and summary feedback is provided to the user. In this regard, the following information is generated and presented to the user via a display screen: person's step distance; speed of a person's movement; how many steps or other movements were performed in a fixed time frame; and/or an avatar reflecting the person's movements in real time with no or minimal jitter or time lagging.

Notably, immediate feedback is provided on accuracy that takes into account all directions of the movement. Summary feedback is more detailed and provides information on movement patterns (trajectories), movement speed, movement distance as well as accuracy. This level of detail is useful for clinical assessment and tracking progress.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods and sequence of steps of the method without departing from the concept, spirit and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

We claim:

1. A method for providing a Digital Health Platform ("DHP") suite for examination and intervention executable on a computing device, comprising:
  running code of the DHP suite on the computing device to facilitate lower extremity tracking in various light conditions and the provision of a DHP examination and intervention software program having a virtual environment and serious games in which a person is to interact with at least one virtual object;
  using the code to obtain tracked data defining tracked movements of at least the person's lower extremities as the person interacts with the DHP examination and intervention software program in the various light conditions;
  increasing an accuracy of at least position data contained in the tracked data by performing combinations of sequential coarse filtering operations and fine filtering operations using the position data;

recreating the person's lower extremity movement in the virtual environment using the position data which has been coarse and fine filtered; and dynamically adjusting a complexity of a first game of the serious games presented to the person based on the person's cognitive and sensory motor performance while performing a previous iteration of the first game, where the person's cognitive and sensory motor performance is at least partially defined by the position data which has been coarse and fine filtered.

2. The method according to claim 1, further comprising using an open source code development kit to implement the code.

3. The method according to claim 1, wherein the tracked data comprises video data and heart rata data in addition to the position data.

4. The method according to claim 3, wherein the tracked data further comprises eye movement data or brain electrical activity data.

5. The method according to claim 1, wherein the coarse and fine filtering operations comprise smoothing, correction, prediction, maximum deviation and jitter radius operations.

6. The method according to claim 5, wherein a jitter radius is a radius of measure taken from an assumed true point and extends to a calculated radius that includes permissible deviations from the assumed true point.

7. The method according to claim 6, wherein the jitter radius encompasses predicted points and trajectories in still and in motion.

8. The method according to claim 1, wherein the coarse and fine filtering operations comprise:
obtaining a positional xyz data point of where the person's body part is expected to be located in a multi-dimensional space;
obtaining a trajectory prediction for the person's body part;
determining if a detected movement match a predicted movement;
mapping the detected movement as a true and accurate trajectory of the person's body part if the detected movement matches a predicted movement; and
disregarding any tracked data that indicates a deviation of a certain degree from the true and accurate trajectory.

9. The method according to claim 1, wherein the tracked data comprises heart rate data that is obtained using at least infrared technology which acquires infrared data for at least one body part of the person.

10. The method according to claim 9, further comprising:
determining a difference between a first infrared pattern defined by the tracked data and a second infrared pattern defined by the tracked data; and
determining the person's current body temperature using the determined difference between the first and second infrared patterns.

11. The method according to claim 9, further comprising:
calculating a first variation in density between adjacent pixels of first infrared data associated with a first data frame and a second variation in density between adjacent pixels of a second infrared data associated with a second data frame;
determining a difference between the first and second variations; and
determining the person's current body temperature using the determined difference between the first and second variations.

12. A system, comprising:
a processor; and
a computer-readable medium comprising programming instructions that are configured to cause the processor to implement a Digital Health Platform ("DHP") examination and intervention process at an electronic device, wherein the programming instructions comprise instructions to:
track lower extremity movement in a low light condition;
execute a DHP examination and intervention software program having a virtual environment and serious games in which a person is to interact with at least one virtual object;
obtain tracked data defining tracked movements of at least the person's lower extremities as the person interacts with the DHP examination and intervention software program in the low light condition;
increase an accuracy of at least position data contained in the tracked data by performing coarse filtering operations and fine filtering operations using the position data;
recreate the person's lower extremity movement in the virtual environment using the position data which has been coarse and fine filtered; and
dynamically adjust a complexity of a first game of the serious games presented to the person based on the person's cognitive and sensory motor performance while performing a previous iteration of the first game, where the person's cognitive and sensory motor performance is at least partially defined by the position data which has been coarse and fine filtered.

13. The system according to claim 12, wherein an open source code development kit is used to implement the programming instructions.

14. The system according to claim 12, wherein the tracked data comprises video data and heart rata data in addition to the position data.

15. The system according to claim 14, wherein the tracked data further comprises eye movement data or brain electrical activity data.

16. The system according to claim 12, wherein the coarse and fine filtering operations comprise smoothing, correction, prediction, maximum deviation and jitter radius operations.

17. The system according to claim 12, wherein the coarse and fine filtering operations comprise:
obtaining a positional xyz data point of where the person's body part is expected to be located in a multi-dimensional space;
obtaining a trajectory prediction for the person's body part;
determining if a detected movement match a predicted movement;
mapping the detected movement as a true and accurate trajectory of the person's body part if the detected movement matches a predicted movement; and
disregarding any tracked data that indicates a deviation of a certain degree from the true and accurate trajectory.

18. The system according to claim 12, wherein the tracked data comprises heart rate data that is obtained using at least infrared technology which acquires infrared data for at least one body part of the person.

19. The system according to claim 18, wherein the programming instructions further comprise instructions to:
determine a difference between a first infrared pattern defined by the tracked data and a second infrared pattern defined by the tracked data; and determine the person's current body temperature using the determined difference between the first and second infrared patterns.

20. The system according to claim 18, wherein the programming instructions further comprise instructions to:
calculate a first variation in density between adjacent pixels of first infrared data associated with a first data frame and a second variation in density between adjacent pixels of a second infrared data associated with a second data frame; and
determine a difference between the first and second variations; and
determining the person's current body temperature using the determined difference between the first and second variations.

21. The method according to claim 1, wherein the person's cognitive and sensory motor performance is at least partially defined by the infrared data.

22. The method according to claim 9, further comprising dynamically adjusting a complexity of a second game of the serious games presented to the person based on the person's cognitive and sensory motor performance while performing a previous iteration of the second game, where the person's cognitive and sensory motor performance is at least partially defined by the infrared data.

23. The method according to claim 1, wherein the first game's complexity is dynamically adjusted based on the person's demographics or predictive mobility deficits.

* * * * *